United States Patent [19]
Davis et al.

[11] Patent Number: 5,670,158
[45] Date of Patent: *Sep. 23, 1997

[54] BISACODYL DOSAGE FORM

[75] Inventors: Paula Denise Davis; Douglas Joseph Dobrozsi; Gary Robert Kelm, all of Cincinnati; Kenneth Gary Mandel, Fairfield, all of Ohio

[73] Assignee: The Procter & Gamble Company, Cincinnati, Ohio

[*] Notice: The term of this patent shall not extend beyond the expiration date of Pat. No. 5,651,983.

[21] Appl. No.: 558,338

[22] Filed: Nov. 15, 1995

Related U.S. Application Data

[63] Continuation of Ser. No. 279,361, Jul. 22, 1994, abandoned, which is a continuation of Ser. No. 23,412, Feb. 26, 1993, abandoned.

[51] Int. Cl.$^6$ .................. A61K 9/00; A61K 31/715; A61K 47/00
[52] U.S. Cl. .................. 424/400; 424/406; 424/408; 424/452; 424/468; 514/58; 514/777; 514/778
[58] Field of Search .................. 424/400, 406, 424/408, 452, 468; 514/58, 777, 778

[56] References Cited

U.S. PATENT DOCUMENTS

| | | | |
|---|---|---|---|
| 2,764,590 | 9/1956 | Kottler | 260/295 |
| 3,927,195 | 12/1975 | Messora | 424/21 |
| 4,810,707 | 3/1989 | Michaelson. | |
| 4,834,985 | 5/1989 | Elger et al. | 424/488 |
| 4,952,402 | 8/1990 | Sparks | 424/419 |
| 5,068,110 | 11/1991 | Fawzi et al. | 424/461 |

FOREIGN PATENT DOCUMENTS

| | | | |
|---|---|---|---|
| 0313845 | 5/1989 | European Pat. Off. | A61K 9/32 |
| 0343575 | 8/1989 | European Pat. Off. | |
| 818022 | 10/1989 | Germany | A61K 9/48 |
| 57-099521 | 6/1982 | Japan | A61K 31/44 |
| 59-193816 | 11/1984 | Japan. | |
| 63/20409 | 4/1988 | Japan. | |
| 63-258815 | 10/1988 | Japan | A61K 47/00 |
| 63-264534 | 11/1988 | Japan. | |
| 2230442 | 10/1990 | United Kingdom | A61J 3/07 |
| 2230441 | 10/1990 | United Kingdom | A61J 3/07 |
| 91/12795 | 9/1991 | WIPO | A61K 9/22 |

OTHER PUBLICATIONS

Schmidt, P.C. and F. Niemann, "The MiniWiD–Coater: II. Comparison of Acid Resistance of Enteric–coated Bisacodyl Pellets Coated with Different Polymers", *Drug Development and Indiustrial Pharmacy*, vol. 18 No. 18 (1992), pp. 1969–1979.

Fincher, J. H., "Particle Size of Drugs and Its Relationship to Absorption and Activity", *Journal of Pharmaceutical Sciences*, vol. 57, No. 11 (Nov., 1968), pp. 1825–1835.

Jauch, R., R. Hankwitz, K. Beschke & H. Pelzer, "Bis–(p–hydroxyphenyl)–pyridyl–2–methane: The Common Laxative Principle of Bisacodyl and Sodium Picosulfate", *Arzneim.–Forsch. (Drug Research)*, vol. 25, No. 11 (1975), pp. 1796–1800.

Kamm, M.A., J.E. Lennard–Jones, D.G. Thompson, R. Sobnack, N.W. Garvie & M. Granowska, "Dynamic Scanning Defines a Colonic Defect in Severe Idiopathic Constipation" *Gut*, vol. 29, (1988), pp. 1085–1092.

Leng–Peschlow, E., "Effects of Sennosides A +B and Bisacodyl on Rat Large Intestine", *Pharmacology*, vol. 38 (1989), pp. 310–318.

Preston, D.M. & J.E. Lennard–Jones, "Pelvic Motility an Response to Intraluminal Bisacodyl in Slow–Transit Constipation", *Digestive Diseases and Sciences*, vol. 30, No. 4 (Apr. 1985), pp. 289–294.

Roth, W. & K. Beschke, "Pharmacokinetics and Laxative Effect of Bisacodyl After Administration of Various Dosage Forms", *Arzneim.–Forsch. (Drug Research)*, vol. 38(I), No. 4 (1988), pp. 570–574.

*Merck Index*, 11th ed. (1989), S. Budavari, ed., No. 1253, p. 193.

*Physician's Desk Reference for Nonprescription Drugs*, 14th ed. (1993), pp. 551–552.

D. Meiren, A. P. Gilev and V. N. Kiseleva, "Bioavailability of Bisacodyl Tablets", *Inst. Org. Sint.*, vol. 11, pp. 134–137. (1985).

*Primary Examiner*—Kevin E. Weddington
*Attorney, Agent, or Firm*—Betty J. Zea; Mick B. Graff; Karen F. Clark

[57] ABSTRACT

The subject invention involves pharmaceutical compositions in dosage unit form, for peroral administration of bisacodyl to a human or lower animal having a gastrointestinal tract, with a lumen therethrough, with a small intestine and a colon with a junction therebetween, comprising:

(a) a safe and effective amount of rapidly-dissolving bisacodyl means; and (b) a delivery means which prevents the release of bisacodyl from the dosage form into the lumen of the gastrointestinal tract during transport of the dosage form through the lumen until the dosage form is near the junction between the small intestine and the colon or in the colon, and which then releases the bisacodyl in the lumen near the junction between the small intestine and the colon or within the colon, The subject invention also involves methods for providing laxation for humans and lower animals in need thereof by peroral administration of such compositions.

13 Claims, No Drawings

BISACODYL DOSAGE FORM

This is a continuation of application Ser. No. 08/279,361, filed on Jul. 22, 1994, now abandoned which is a continuation of application Ser. No. 08/023,412, filed on Feb. 26, 1993 now abandoned.

The subject invention involves a novel dosage form of bisacodyl for providing laxation in the colon.

BACKGROUND OF THE INVENTION

Bisacodyl, 4,4'-(2-pyridylmethylene)bisphenoldiacetate, is disclosed in the *Merck Index*, 11th ed. (1989), S. Budavari, ed., No. 1253, p. 193. Enteric coated bisacodyl tablets indicted for the relief of constipation are disclosed in the *Physician's Desk Reference for Non Prescription Drugs*, 13th ed. (1992), p. 550. Release of bisacodyl in the colon (large intestine) as a preferred mode of delivery of the drug in order to minimize systemic absorption of bisacodyl is disclosed in Roth, W. & K. Beschke, "Pharmacokinetics and Laxative Effect of Bisacodyl after Administration of Various Dosage Forms", *Arzneim.-Forsch./Drug Res.*, Vol. 38(I), No. 4 (1988), pp. 570–574. Other references which describe the activity of bisacodyl include Jauch, R., R. Hankwitz, K. Beschke, & H. Pelzer, "Bis-(p-hydroxyphenyl)-pyridyl-2-methane: The Common Laxative Principle of Bisacodyl and Sodium Picosulfate", *Arzneim.-Forsch./Drug Res.*, Vol. 25, No. 11 (1975), pp. 1796–1800; Kamm, M. A., J. E. Lennard-Jones, D. G. Thompson, R. Sobnack, N. W. Garvie & N. Granowska, "Dynamic Scanning Defines a Colonic Defect in Severe Idiopathic Constipation", *Gut*, Vol. 29 (1988), pp. 1085–1092; Preston, D. E. & J. E. Lennard-Jones, "Pelvic Motility and Response to Intraluminal Bisacodyl in Slow-Transit Constipation", *Digestive Diseases and Sciences*, Vol. 30, No. 4 (1985), pp. 289–294; Leng-Peschlow, E., "Effect of Sennosides A+B and Bisacodyl on Rat Large Intestine", *Pharmacology*, Vol. 38 (1989), pp. 310–318. Secondary diarrhea or repeat bowel movements is one of several undesirable side effects which patients using bisacodyl commonly experience.

It is an object of the subject invention to provide a dosage form of bisacodyl which provides laxation efficacy to patients without the occurrence of significant side effects such as substantial secondary diarrhea.

It is a further object of the subject invention to provide therapeutic laxation activity at substantially lower doses than is required with known peroral dosage forms of bisacodyl.

SUMMARY OF THE INVENTION

The subject invention involves pharmaceutical compositions in dosage unit form, for peroral administration of bisacodyl to a human or lower animal having a gastrointestinal tract, with a lumen therethrough, with a small intestine and a colon with a junction therebetween, comprising:

(a) a safe and effective amount of rapidly-dissolving bisacodyl means; and (b) a delivery means which prevents the release of bisacodyl from the dosage form into the lumen of the gastrointestinal tract during transport of the dosage form through the lumen until the dosage form is near the junction between the small intestine and the colon or in the colon, and which then releases the bisacodyl in the lumen near the junction between the small intestine and the colon or within the colon.

DETAILED DESCRIPTION OF THE INVENTION

Bisacodyl is an inactive prodrug that is hydrolyzed by intestinal brush border enzymes and colonic bacteria to desacetyl bisacodyl which is the active species. Contact of the desacetyl bisacodyl with the mucosa of the colon stimulates sensory nerve endings to produce increased propulsive peristaltic contractions of the colon which accelerate movement of contents through the colon. Administration of bisacodyl has also been shown to promote fluid and ion accumulation in the colon, which increases its laxative effect. Both bisacodyl and desacetyl bisacodyl are poorly water soluble with absorption reported from both the small intestine and colon. Absorption from the small intestine may be greater than from the colon.

Since desacetyl bisacodyl acts upon contact with the lumenal mucosa of the colon, its laxative effect is dependent upon generation of sufficient levels of the drug in the lumen of the colon. However, it has been found that secondary diarrhea associated with peroral administration of bisacodyl is at least partially due to biliary recirculation of conjugates of absorbed desacetyl bisacodyl which induce further laxation when cleaved by colonic bacteria to desacetyl bisacodyl. Therefore, it has been found desirable to minimize colonic absorption of desacetyl bisacodyl from the original peroral dose of bisacodyl while achieving therapeutically effective levels of the drug in the lumen of the colon.

Delivery of suspensions or solutions of bisacodyl to the colon results in laxation. It has been surprisingly discovered that delivery of bisacodyl to the colon as a suspension of very fine, rapidly dissolving particles, or in a solubilized form, produces maximal laxation at doses which do not evoke secondary episodes of diarrhea. In contrast, delivery to the colon of a suspension of more slowly dissolving commercially available bisacodyl requires significantly higher doses to produce maximal laxation; and at the doses which produce maximal laxation, the more slowly dissolving commercially available bisacodyl also evokes secondary episodes of diarrhea. It has also been found that there is a direct relationship between cumulative bisacodyl dissolution and acceleration of colonic transit, a measure of laxative efficacy.

Although the subject invention is not limited to a particular mechanism, it is believed that the elimination of secondary diarrhea for colonically delivered doses of rapidly dissolving bisacodyl which are maximally effective for laxation is due to significantly reduced absorption and subsequent biliary recirculation of bisacodyl-derived compounds. This appears to occur with rapidly dissolving bisacodyl even though increasing the dissolution rate of a poorly soluble drug usually increases absorption (see, for example, Fincher, J. H., "Particle Size of Drugs and Its Relationship to Absorption and Activity", *J. Pharm. Sci.*, Vol. 57, No. 11 (1968), p. 1825). Reduced absorption is believed to be the result of one or more of colonic delivery of bisacodyl, a lower dose of bisacodyl, rapid attainment of therapeutic drug levels in the lumen of the colon due to rapid dissolution, and the laxative effect of the drug which serves to evacuate unabsorbed drug from the colon.

The subject invention involves pharmaceutical compositions in dosage unit form, for peroral administration of bisacodyl to a human or lower animal having a gastrointestinal tract, with a lumen therethrough, comprising a small intestine and a colon with a junction therebetween, comprising:

(a) a safe and effective amount of rapidly-dissolving bisacodyl means; and (b) a delivery means which prevents the release of bisacodyl from the dosage form into the lumen of the gastrointestinal tract during transport of the dosage form through the lumen to near or into the colon, and which releases the bisacodyl means in the lumen near the junction between the small intestine and the colon or within the colon.

The methods and compositions of the subject invention comprise a safe and effective amount of bisacodyl. The phrase "safe and effective amount", as used herein, means an amount of bisacodyl high enough to provide a significant positive modification of the condition to be treated, but low enough to avoid serious side effects (at a reasonable benefit/ risk ratio), within the scope of sound medical judgment. A safe and effective amount of bisacodyl will vary with the particular condition being treated, the age and physical condition of the patient being treated, the severity of the condition, the duration of the treatment, the nature of concurrent therapy and like factors. As indicated hereinabove, an effective dose of bisacodyl in compositions of the subject invention is preferably substantially lower than the dose of bisacodyl required to achieve efficacy with conventional bisacodyl compositions.

A safe and effective dose of bisacodyl in a composition of the subject invention preferably provides from about 0.1 mg to about 50 mg of bisacodyl locally to the lumen of the lower gastrointestinal tract near the junction of the small intestine and colon or within the colon of a human patient. A preferred amount of bisacodyl dosed to a human patient is from about 0.2 mg to about 30 mg; more preferred is from about 0.5 mg to about 15 mg; more preferred still is from about 0.8 mg to about 10 mg; still more preferred is from about 1 mg to about 5 mg; also preferred is less than about 3 mg; also preferred is less than about 1 mg. A dosage unit form of the subject invention preferably contains a single dose of bisacodyl in the above amounts.

A dosage unit form of a composition of the subject invention comprises two functional parts: (1) a rapidly-dissolving bisacodyl means; and (2) a delivery means that delays the release of the bisacodyl until the dosage form has been transported through the gastrointestinal tract to a point near the junction of the small intestine and colon or within the colon.

As used herein, "rapidly-dissolving bisacodyl means" or "bisacodyl means" is bisacodyl in a physical form or composition which enhances the rate of dissolution of bisacodyl in the intestinal juices in the lumen of the colon compared to conventional bisacodyl formulations. As used herein, "conventional bisacodyl formulations" are solid dosage forms of bisacodyl made with commercially-available bisacodyl having a mean particle size of about 25 µm effective diameter or greater. Commercially-available bisacodyl compositions are typically coated with an enteric polymer or combination of polymers that is insoluble at pH's below about 6.5. An example of such a product is Dulcolax® (Boehringer Ingelheim Pharmaceuticals, Ridgefield, Conn.).

A preferred rapidly-dissolving bisacodyl means of the subject invention comprises micronized bisacodyl. Preferably substantially all of the bisacodyl in certain compositions of the subject invention is micronized bisacodyl. As used herein, "micronized bisacodyl", means solid bisacodyl which is finely divided. The particle size distribution of micronized bisacodyl is preferably such that greater than 90% of the particles are less than 10 µm in effective diameter, more preferably greater than 95% are less than 10 µm in effective diameter, more preferably still greater than 99% are less than 10 µm in effective diameter. As used herein, "effective diameter" means the mean volume diameter, which is equivalent to the diameter of a sphere of equal volume to the particle being measured.

It has been found that micronized bisacodyl, when formulated into common dosage forms, such as tablets and capsules, dissolves rapidly in the intestinal juices of the colon compared to conventional bisacodyl formulations of similar dosage forms.

Another preferred rapidly-dissolving bisacodyl means is comprised of an inclusion complex of bisacodyl and a cyclodextrin. Preferably substantially all of the bisacodyl in certain compositions of the subject invention is incorporated in such inclusion complexes. As used herein, "cyclodextrin", means a cyclic carbohydrate molecule composed of six, seven, or eight glucose monomers arranged in a donut shaped ring which are termed $\alpha$-, $\beta$-, and $\gamma$-cyclodextrin, respectively. See Pitha, J., L. Szente & J. Szejtli, "Molecular Encapsulation of Drugs by Cyclodextrins and Congeners", *Controlled Drug Delivery*, Vol. 1, S. D. Brunk, ed., CRC Press, Inc., Boca Raton, Fla., 1983. These molecules may also be modified by the addition of substituents such hydroxypropyl groups to the hydroxyl groups of the glucose monomers on the outside of the ring. As used herein, "inclusion complex" means a complex between one or more bisacodyl molecules and one or more cyclodextrin molecules in which all or a portion of the bisacodyl molecule or molecules resides in the cavity or cavities of the cyclodextrin molecule or molecules without the formation of a covalent bond between the bisacodyl and cyclodextrin molecules. The molecular ratio of cyclodextrin to bisacodyl preferably ranges from about 0.5 to about 30. Mixtures of cyclodextrins may also be used. Such complexes of cyclodextrin and bisacodyl may be prepared by any of a number of means well known to those skilled in the art, such as solubilization of bisacodyl in an aqueous solution of the cyclodextrin followed by spray drying or lyophilization of the resulting solution to produce a dry powder of the inclusion complex.

Another preferred rapidly-dissolving bisacodyl means is comprised of a solid dispersion of bisacodyl in a water-soluble carrier such as polyethylene glycol (molecular weight greater than about 1000 daltons), poloxamer, citric acid, tartaric acid, dextrose monohydrate, or urea. Preferably substantially all of the bisacodyl in certain compositions of the subject invention is incorporated in such solid dispersions. Typical ratios (weight:weight) of water soluble carrier to bisacodyl range from about 1:1 to about 20:1. The solid dispersions may be prepared by a number of techniques well known to those skilled in the ad, such as solvent evaporation, melt, spray drying, or freeze drying. The solvent evaporation technique involves dissolution of both the water-soluble carrier and bisacodyl in a volatile solvent which is then removed by evaporation or spray drying. The melt technique involves preparation of a melt of the water-soluble carrier and bisacodyl followed by solidification to produce a solid which may then be granulated. Aqueous or aqueous/water miscible solvent solutions of the water-soluble carrier and bisacodyl may also be prepared and either spray dried or lyophilized to produce a solid dispersion. Preferred water soluble carriers are those which are also solvents for bisacodyl, such as polyethylene glycol. Such solid dispersions are preferably incorporated into the dosage unit form as solid particulates, preferably less than about 1 mm in diameter.

Another preferred rapidly-dissolving bisacodyl means is comprised of a solution of bisacodyl in a water-miscible, pharmaceutically-acceptable solvent that is liquid at body temperature (about 37° C). Preferably substantially all of the bisacodyl in certain compositions of the subject invention is incorporated in such solutions. A preferred solvent for such solutions is polyethylene glycol (molecular weight less than about 1000 daltons). The amount of bisacodyl present in such solution will be a function of the particular solvent, but concentrations typically range from about 0.5% to about 30%, preferably from about 1% to about 20%, more preferably from about 5% to about 15%.

Another preferred rapidly-dissolving bisacodyl means is a self-emulsifying or self-dispersing lipid solution of bisacodyl.

Preferably substantially all of the bisacodyl in certain compositions of the subject invention is incorporated in such lipid solutions. The lipid in which bisacodyl is dissolved comprises, preferably consists essentially of, a surfactant or mixture of surfactants, the lipid having the following properties: (a) being a homogeneous liquid at 37° C., (b) having an HLB of from about 6 to about 18, and (c) forming a stable dispersion in water at 20° C. at a concentration of 10%. Preferred lipids also have the following properties: (d) being soluble in isopropanol at 20° C. at a concentration of 10%, and (e) being soluble in cottonseed oil at 20° C. at a concentration of 1%.

As used herein, HLB refers to the hydrophilic/lipophilic balance of the molecule as described in Griffin, W. C., "Classification of Surface-Active Agents by 'HLB'", *Journal of the Society of Cosmetic Chemistry*, Vol. 1, No. 5 (1949), p. 311. The HLB of the lipid is preferably from 10 to 16.

The level of bisacodyl in such lipid solution preferably is from about 0.5% to about 30%, more preferably from about 1% to about 20%, more preferably still from about 5% to about 15%. Preferred examples of surfactants which can be used in compositions of the subject invention include the following: polyoxyethylene sorbitan monoesters such as polysorbate 80* and polysorbate 81* available from ICI Americas, Inc., Wilmington, Del., PEG-25 glyceryl trioleate* available from Goldschmidt Chemical Corp., Hopewell, Va.; block copolymers of ethylene oxide and propylene oxide such as poloxamer 182*, poloxamer 183* and poloxamer 184* available from BASF Corp., Parsippany, N.J., polyoxyl 35 castor oil** available from BASF Corp.; and polyglycerol oleate esters such as polyglycerol-3 oleate available from Capitol City Products Company, Columbus, Ohio; and mixtures thereof. (*See CTFA Cosmetic Ingredient Dictionary, Third Edition (1984), N. F. Estrin, P. A. Crosely & C. R. Haynes, Editors, The Cosmetic, Toiletry and Fragrance Association, Inc., Washington, D.C. **See The National Formulary, 17th Edition (1990), The United States Pharmacopeial Convention, Inc., Rockville, Md.)

The lipid of the compositions of the subject invention may also comprise a lipophilic solvent for bisacodyl. Preferred lipophilic solvents are triglycerides or mixtures of triglycerides having fatty chains from about 2 to 6 carbon atoms. Other preferred lipophilic solvents include mono- and di-glycerides with saturated straight fatty chains from about 2 to 10 carbon atoms, or unsaturated straight chains of from about 12 to 18 carbon atoms, or mixtures thereof. Still other preferred lipophilic solvents are tri-esters of citric acid having fatty chains from about 2 to 4 carbon atoms.

Preferred compositions of the subject invention which have lipids which are mixtures of lipophilic solvents and surfactants have lipids comprising, preferably consisting essentially of, from about 25% to about 85% of the lipophilic solvent, and from about 15% to about 75% of the surfactant; more preferably from about 40% to about 70% of the lipophilic solvent, and from about 30% to about 60% of the surfactant.

Preferred examples of lipids which are mixtures of lipophilic solvents and surfactants include the following: caprylic/capric triglyceride PEG-4 complex, and glyceryl caprylate/caprate and PEG-8 caprylate/caprate, available from Gattefosse Corp., Elmsford, N.Y.

Another lipid solution useful in the subject invention involves compositions having a lipid comprising triglycerides interesterified with polyethylene glycol. These materials are liquid at 37° C. and have an HLB in the range of from about 3 to about 7, preferably from 5 to 7.

Preferred examples of such materials are glycolysed ethoxylated glycerides obtained by partial alcoholysis of natural vegetable oils, e.g., those available under the trade name Labrafil® from Gattefosse Corp., Elmsford, N.Y. A preferred example of such material is Labrafil 2609®, glycolysed ethoxylated glycerides obtained by partial alcoholysis of corn oil with polyethylene glycol 400.

The bisacodyl means can comprise, in addition to the preceding rapidly-dissolving preparations of bisacodyl, excipients which improve the performance of the bisacodyl means. Such additional components may include, for example, dispersants which help disperse the bisacodyl in the gastrointestinal juices to aid in the rapid dissolution of the bisacodyl. Examples of such dispersants include surfactants with an HLB of greater than about 15. Other optional components include preservatives, stabilizers, materials for facilitating the manufacture of the dosage form, and other excipients.

Preferred bisacodyl means of the subject invention which comprise solid particulate forms of bisacodyl described above, e.g., micronized bisacodyl, bisacodyl:cyclodextrin inclusion complexes, or granulated solid dispersions, that are encapsulated in a hard gelatin capsule or compressed into a tablet. Such bisacodyl particulate solids may be blended with various excipients such as diluents (e.g., lactose, sucrose, glucose, starch, calcium sulfate, dicalcium phosphate, micro crystalline cellulose); binders (e.g., polyvinylpyrrolidone, pre-gelatinized starch, gelatin, hydroxypropyl methylcellulose, methylcellulose, hydroxyethyl cellulose, hydroxypropyl cellulose); lubricants (e.g., stearic acid, magnesium stearate); disintegrants (e.g., sodium starch glycolate, cross-linked polyvinylpyrrolidone, cross-linked carboxymethyl cellulose); glidants (e.g., fumed silica); and buffers. The solids mixture may be prepared via a number of techniques well-known to pharmaceutical science such as dry mixing, wet granulation, and fluid bed granulation, and be filled into capsules or compressed into tablets using conventional equipment and processes. Any compressed tablet preferably is made such that it rapidly disintegrates in intestinal juices.

Preferred bisacodyl means of the subject invention which comprise liquid forms of bisacodyl described above, e.g., bisacodyl in a water-miscible liquid solvent, bisacodyl in a lipid solution, or a melted solid dispersion of bisacodyl, are filled into hard or soft elastic gelatin (SEG) capsules using conventional equipment and processes.

In the compositions of the subject invention, the delivery means prevents the release of bisacodyl as the dosage form passes through the upper gastrointestinal tract, including the mouth, esophagus, stomach, and small intestine, until the dosage form is near the junction between the small intestine and the colon or is in the colon. This precludes systemic absorption of bisacodyl and/or desacetyl bisacodyl from the upper gastrointestinal tract (and subsequent biliary excretion of metabolic conjugates), and/or dilution of the released bisacodyl in the contents of the upper gastrointestinal tract (which results in a less concentrated dose of the drug reaching the site of activity in the colon). Therefore, the delivery means in combination with the rapidly dissolving bisacodyl means, provides a method of delivering bisacodyl in a concentrated form to the colon. This results in more effective laxation and reduced absorption of bisacodyl and/or its metabolites and the subsequent manifestation of secondary diarrhea produced by biliary excretion of metabolic conjugates.

As used herein, "delivery means", is a material or materials which completely surround and encase the bisacodyl means in the dosage unit form prior to oral administration. Delivery means contemplated for the subject invention compositions are comprised of, or consist essentially of, for example, coatings encasing conventional tablets or capsules. Delivery means may also be comprised of, or consist essentially of, the shells of capsules. Delivery means may also be comprised of, or consist essentially of, pulse capsules.

The delivery means is selected such that the bisacodyl means will be released at about the time that the dosage form reaches the junction between the small intestine and the colon, or thereafter in the colon. Delivery means which can be utilized to achieve this result include coatings or coverings applied to conventional dosage forms comprising the bisacodyl means such as compressed tablets, hard gelatin capsules, and soft elastic gelatin capsules. Preferred coating materials include pH-sensitive materials, which remain intact in the lower pH environs of the stomach and small intestine, but which disintegrate or dissolve at the pH commonly found in the latter portion of the small intestine or beginning of the colon of the patient. Suitable coatings can also be made of materials which are affected little by changes in pH, but which dissolve or erode slowly as the dosage unit form passes through the gastrointestinal tract; the thickness of such delivery means is selected such that the delivery means breeches, releasing the bisacodyl means, after the approximate time required for the dosage form to reach the colon. Coatings made from materials or mixtures of materials which combine aspects of the pH-release and time dependent-release mechanisms described in this paragraph are also suitable. A preferred delivery means which combines the pH-release and time dependent-release mechanisms comprises an outer coating of pH sensitive material which dissolves at the pH typical of the upper small intestine (duodenum) but not at lower pH, and an inner coating of pH-insensitive, erodable material of a thickness such that the inner coating breaches after the approximate time required for the dosage unit form to pass through the length of the small intestine.

Another delivery means of the subject invention comprises, or consists essentially of, capsule shells prepared from materials which exhibit the pH-release and time dependent-release mechanisms described in the preceding paragraph, or combinations thereof. Such capsule shells may then be used to encapsulate the bisacodyl means.

Another delivery means of the subject invention comprises, or consists essentially of, pulse capsules. As used herein, "pulse capsules" include capsules described in U.K. Patent Application Nos. 2,230,441A and 2,230,442A of National Research Development Corporation, published Oct. 24, 1990; and PCT Patent Application No. WO 91/12795 of National Research Corporation, published Sep. 5, 1991, all of which have U.S. patent application equivalents and are incorporated herein by reference. Preferred pulse capsules comprise, or consist essentially of, a water-insoluble male capsule shell, a water-dispersible or swellable hydrophilic plug, and a water-soluble female capsule shell. The male and female shells preferably have the size, shape, and fit of conventional hard gelatin capsule male and female mating shells.

For preferred pulse capsule dosage unit form compositions of the subject invention, the bisacodyl means is contained in the male capsule shell with the hydrophilic plug blocking the entire opening of the male shell. The female shell covers the exposed portion of the plug and extends along the outer cylindrical surface of the male shell.

Upon contact with the fluids of the gastrointestinal tract, the female shell of a pulse capsule dissolves and the hydrophilic plug begins to hydrate. The composition and size of the hydrophilic plug is selected such that the hydrophilic plug will disengage from the male capsule shell releasing the bisacodyl means at the approximate time when the dosage form reaches the colon.

A preferred pulse capsule delivery means additionally comprises a pH sensitive material that will dissolve at a pH typically associated with the upper small intestine (duodenum). This will delay dissolution of the female capsule shell and initiation of hydration of the hydrophilic plug until the dosage unit form has emptied from the stomach. This eliminates variability due to gastric emptying time when determining the elapsed time desired between dissolution of the female shell and release of the bisacodyl means due to disengagement of the plug from the male shell opening.

Various delivery means described above are preferably prepared by coating a conventional tablet, hard gelatin capsule, soft gelatin capsule or pulse capsule comprising the bisacodyl means with one or more materials that will dissolve/disperse at desired points in the small intestine or colon. Coating aids such as plasticizers and talc may be incorporated into the coating compositions. Compressed tablets, and soft and hard gelatin capsules are typically coated in fluidized bed equipment. Tablets and capsules are also typically coated in perforated pans. Tablets may also be coated via compression coating.

Preferred coating materials useful for preparing delivery means for the dosage unit form compositions of the subject invention include pH-sensitive polymers, such as polymethacrylates (e.g., Eudragit® Type S, or combinations of Eudragit® Typos L and S, Rohm Pharma, Darmstadt, West Germany), hydroxypropyl methylcellulose phthalate, and shellac, all of which are insoluble at the pH of the gastric environment, but will dissolve at various pHs above about pH 6.5. The pH at which such pH-sensitive polymers begin to dissolve and the thickness of coat will determine the site in the intestinal lumen at which the bisacodyl means is released. Typically, higher pH dissolution points and increased amounts of pH-sensitive polymer will increase the distance the dosage unit form will travel in the small intestine and colon prior to release of the bisacodyl. For certain compositions of the subject invention, preferred pH-sensitive enteric materials dissolve only at a pH of greater than about 6.5, more preferred enteric materials dissolve only at pH of greater than about 6.8; also preferred are enteric materials which dissolve only at a pH of greater than about 7. An especially preferred pH-sensitive material is a polymethacrylate polymer (Eudragit® S) with a pH dissolution value of about pH 7.

Additional preferred dosage unit form compositions of the subject invention are conventional tablets, hard gelatin capsules, or soft elastic gelatin capsules comprising the bisacodyl means, having an inner coating of a time dependent-release coating and an outer coating of an enteric material or combination of enteric materials which remain intact in the lower pH environs of the stomach, but which disintegrate or dissolve at the pH commonly found in the upper portion of the small intestine (duodenum).

Preferred enteric coating materials suitable for compositions include pH-sensitive polymers, such as polymethacrylates (e.g., Eudragit Types L and L-55, Rohm Pharma, Darmstadt, West Germany), cellulose acetate phthalate, hydroxypropyl methylcellulose phthalate, and polyvinyl acetate phthalate, which are insoluble at the pH of the gastric environment, but will dissolve at various pH's above about pH 5 and less than about 6.5. The purpose of the enteric coating of these compositions is to delay the start of dissolution/erosion of the time dependent-release coating until the dosage form has emptied from the stomach.

Preferred time dependent-release coating materials for such compositions include cellulosic derivatives, such as methyl cellulose, carboxymethyl cellulose, hydroxyethyl cellulose, hydroxypropyl cellulose, and hydroxypropyl methylcellulose. The dissolution rate of these and other time dependent-release materials is largely pH independent and will be a function of molecular weight and degree of substituent substitution. The thickness of the layer of timed-release material, coating conditions, and type and level of coating aids may also influence the rate of dissolution of the coatings. The rate of dissolution of the time dependent-release material in combination with the intestinal transit rate of the dosage unit form will control the site in the intestinal lumen at which the bisacodyl means is released.

The compositions of the subject inventions can optionally include active drug ingredients in addition to bisacodyl. Non-limiting examples of other active drug agents and amounts typically present in such compositions include the following: ducosate sodium, calcium or potassium, from about 5 mg to about 500 mg, preferably from about 50 mg to about 250 mg; glycyrrhiza extract comprising from about 5% to about 30%, preferably from about 10% to about 16%, glycyrrhizic acid, from about 2 mg to about 200 mg, preferably from about 20 mg to about 100 mg; aloe, from about 50 mg to about 500 mg, preferably from about 195 mg to about 325 mg; peppermint oil, from about 250 mg to about 4000 mg, preferably from about 500 mg to about 2500 mg; poloxamer 188, from about 10 mg to about 500 mg, preferably from about 100 mg to about 250 mg; ginger, from about 650 mg to about 1300 mg; mineral oil, USP, from about 500 mg to about 40 g; preferably from about 800 mg to about 20 g; castor oil, USP, from about 500 mg to about 60 g; preferably from about 1 g to about 45 g; and magnesium hydroxide, from about 500 mg to about 5 g, preferably from about 1 g to about 2.8 g.

Another aspect of the subject invention is methods for providing laxation for humans and lower animals in need thereof by peroral administration of the above-described compositions. Conditions for which such laxation may beneficially be provided include the following: constipation, adjunctive therapy for irritable bowel syndrome, and bowel cleansing prior to diagnostic or surgical procedures.

An advantage of providing bisacodyl to patients using the subject compositions is that laxation benefits are generally achieved without the secondary diarrhea commonly associated with conventional bisacodyl compositions. Another advantage is that such laxation benefits are often achieved more quickly than with conventional bisacodyl compositions.

Dosages of the compositions of the subject invention described hereinabove are preferably administered when laxation is needed. One dose is often sufficient to provide the needed laxation, but several dosages can be used sequentially when needed. Such sequential doses are preferably provided to a patient from about 8 hours to about 24 hours apart, up to a maximum of about 4 such dosages.

The following non-limiting examples provide typical formulations for compositions of the subject invention, and typical methods for treating human disorders with such compositions.

EXAMPLE 1

| Bisacodyl Means | | Delivery Means | |
|---|---|---|---|
| Component | mg/unit dose | Component | mg/unit dose |
| Micronized Bisacodyl | 5.0 | Polymethacrylates (Eudragit S-100®) | 8.7 |
| Lactose | 0.5 | Dibutyl Phthalate | 1.7 |
| Dextrates | 25.0 | Talcum | 2.3 |
| Crospovidone | 5.0 | Ferric Oxide | 1.3 |
| Croscarmellose | 5.0 | (Isopropyl Alcohol) | N/A |
| Pregelatinized Starch | 15.0 | | |
| Microcrystalline cellulose | 48.1 | | |
| Magnesium Stearate | 0.4 | | |

BISACODYL MEANS

Micronized bisacodyl is prepared by blending commercially available bisacodyl with lactose and subsequently milling in a fluid energy mill (e.g., Micron Master 01-SDG, The Jet Pulverizer Co.) using conditions that reduce greater than 99% of the particles to an effective diameter of less than about 10 µm. This micronized material is then mixed in a conventional solids blender with dextrates followed by addition of a preblended mixture of microcrystalline cellulose, crospovidone, croscarmellose, pregelatinized starch, and fumed silica. Magnesium stearate is then added to the mixture with additional mixing. The resulting powder blend is compressed into tablets using conventional equipment.

DELIVERY MEANS

Eudragit S-100® and dibutyl phthalate are dissolved into isopropyl alcohol. Talcum and ferric oxide are subsequently added to the solution followed by homogenization using an Ultra Turax T25, IKA Labortechnik. The resulting suspension is then applied to the compressed tablets of the bisacodyl means using a perforated pan coater.

EXAMPLE 2

| Bisacodyl Means | | Delivery Means | |
|---|---|---|---|
| Component | mg/unit dose | Component | mg/unit dose |
| Micronized Bisacodyl | 5.0 | Polymethyacrylates (Eudragit S-100®) | 8.7 |
| Lactose | 0.2 | Dibutyl Phthalate | 1.7 |
| Dextrates | 25.0 | Talcum | 2.3 |
| | | Ferric Oxide | 1.3 |
| | | (Isopropyl Alcohol) | N/A |

BISACODYL MEANS

Micronized bisacodyl is prepared by blending commercially available bisacodyl with lactose and subsequently milling in a fluid energy mill using conditions that reduce greater than 99% of the particles to an effective diameter less than about 10 µm. The micronized material is blended with dextrates and filled into a hard gelatin capsule using conventional equipment.

DELIVERY MEANS

Eudragit S-100® and dibutyl phthalate are dissolved into isopropyl alcohol. Talcum and ferric oxide are subsequently added to the solution followed by homogenization. The resulting suspension is then applied to the hard gelatin capsules of the bisacodyl means using a perforated pan coater.

EXAMPLE 3

| Bisacodyl Means | | Delivery Means | |
|---|---|---|---|
| Component | mg/unit dose | Component | mg/unit dose |
| Hydroxypropyl-β-Cyclodextrin (Encapsin HPB ®, American Maize-Products Co., Hammand, IN) | 150.0 | Polymethacrylates (Eudragit S-100 ®) | 8.7 |
| Bisacodyl | 3.0 | Dibutyl Phthalate | 1.7 |
| | | Talcum | 2.3 |
| | | Ferric Oxide | 1.3 |
| | | (Isopropyl Alcohol) | N/A |

BISACODYL MEANS

Hydroxypropyl-β-cyclodextrin is dissolved in water followed by addition of bisacodyl. The resulting solution/suspension is then spray dried to produce a powder consisting, in part, of an inclusion complex of bisacodyl in hydroxypropyl-β-cyclodextrin. The powder is then filled into a hard gelatin capsule using conventional equipment.

DELIVERY MEANS

Eudragit S-100® and dibutyl phthalate are dissolved into isopropyl alcohol. Talcum and ferric oxide are subsequently added to the solution followed by homogenization. The resulting suspension is then applied to the hard gelatin capsules of the bisacodyl means using a fluid bed coater equipped with a Wurster insert.

EXAMPLE 4

| Bisacodyl Means | | Delivery Means | |
|---|---|---|---|
| Component | mg/unit dose | Component | mg/unit dose |
| Bisacodyl | 1.0 | Polymethacrylates (Eudragit S-100 ®) | 8.7 |
| Polyethylene Glycol 400 | 100.0 | Dibutyl Phthalate | 1.7 |
| | | Talcum | 2.3 |
| | | Ferric Oxide | 1.3 |
| | | (Isopropyl Alcohol) | N/A |

BISACODYL MEANS

Bisacodyl is dissolved into polyethylene glycol 400 with mild heat. The resulting solution is then filled into a soft elastic gelatin capsule using conventional equipment.

DELIVERY MEANS

Eudragit S-100® and dibutyl phthalate are dissolved into isopropyl alcohol. Talcum and ferric oxide are subsequently added to the solution followed by homogenization. The resulting suspension is then applied to the soft elastic gelatin capsules of the bisacodyl means using a fluid bed coater equipped with a Wurster insert.

EXAMPLE 5

| Bisacodyl Means | | Delivery Means | |
|---|---|---|---|
| Component | mg/unit dose | Component | mg/unit dose |
| Labrafil ® 2609 (Gattefossé Corp., Westwood, NJ) | 200.0 | Polymethacrylates (Eudragit S-100 ®) | 8.7 |
| Bisacodyl | 5.0 | Dibutyl Phthalate | 1.7 |
| | | Talcum | 2.3 |
| | | Ferric Oxide | 1.3 |
| | | (Isopropyl Alcohol) | N/A |

BISACODYL MEANS

Bisacodyl is dissolved into Labrafil® 2609 with mild heat. The resulting solution is then filled into a soft elastic gelatin capsule.

DELIVERY MEANS

Eudragit S-100® and dibutyl phthalate are dissolved into isopropyl alcohol. Talcum and ferric oxide are subsequently added to the solution followed by homogenization. The resulting suspension is then applied to the soft elastic gelatin capsules of the bisacodyl means using a fluid bed coater equipped with a Wurster insert.

EXAMPLE 6

| Bisacodyl Means | | Delivery Means | |
|---|---|---|---|
| Component | mg/unit dose | Component | mg/unit dose |
| Micronized Bisacodyl | 5.0 | Pulse Capsule | N/A |
| Lactose | 0.2 | | |
| Dextrates | 25.0 | | |

BISACODYL MEANS

Micronized bisacodyl is prepared by blending commercially available bisacodyl with lactose and subsequently milling in a fluid energy mill using conditions that reduce greater than 99% of the particles to an effective diameter less than about 10 μm. The micronized material is blended with the dextrates.

DELIVERY MEANS

The bisacodyl means is filled into a pulse capsule (Pulsincap®, Scherer DDS, Ltd.) designed to release its contents approximately eight hours following contact with the contents of the gastrointestinal tract.

EXAMPLE 7

| Bisacodyl Means | | Delivery Means | |
|---|---|---|---|
| Component | mg/unit dose | Component | mg/unit dose |
| Labrafil® 2609 (Gattefosse Corp., Westwood, NJ) | 200.0 | Pulse Capsule | N/A |
| Bisacodyl | 5.0 | Cellulose Acetate Phthalate | 5.0 |
| | | Castor Oil | 1.2 |
| | | (Acetone) | N/A |

BISACODYL MEANS

Bisacodyl is dissolved in Labrafil® 2609 with mild heat.

DELIVERY MEANS

The bisacodyl means is filled into a pulse capsule (Pulsincap®) designed to release its contents approximately six hours following contact with the contents of the gastrointestinal tract. Cellulose acetate cellulose and castor oil are dissolved into acetone and the resulting solution is coated on the pulse capsules of the bisacodyl means using a perforated pan coater, thus providing a pH-sensitive coating that dissolves when the dosage unit form reaches the upper small intestine.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A pharmaceutical composition in dosage unit form, for peroral administration of bisacodyl to a human or lower animal having a gastrointestinal tract, with a lumen therethrough, with a small intestine and a colon with a junction therebetween, comprising:

(a) from about 0.1 mg. to about 15 mg. of rapidly-dissolving bisacodyl means; and (b) a delivery means which prevents the release of bisacodyl from the dosage form into the lumen of the gastrointestinal tract during transport of the dosage form through the lumen until the dosage form is near the junction between the small intestine and the colon or in the colon, and which then releases the bisacodyl in the lumen near the junction between the small intestine and the colon or within the colon;

wherein the delivery means is a material or materials which completely surround or encase the rapidly dissolving bisacodyl means in the dosage unit form prior to oral administration.

2. The composition of claim 1 wherein the bisacodyl means comprises micronized bisacodyl, the micronized bisacodyl having a particle size distribution such that greater than 90% of the particles are less than 10 μm in effective diameter.

3. The composition of claim 1 wherein the bisacodyl means comprises from about 0.5 mg to about 15 mg of micronized bisacodyl, the micronized bisacodyl having a particle size distribution such that greater than 99% of the particles are less than 10 μm in effective diameter.

4. The composition of claim 3 wherein the bisacodyl means comprises from about 0.8 mg to about 3 mg of micronized bisacodyl.

5. The composition of claim 3 wherein the bisacodyl means is in the form of a compressed tablet.

6. The composition of claim 3 wherein the bisacodyl means is in the form of a solids-filled hard gelatin capsule.

7. The composition of claim 3 wherein the delivery means comprises a pulse capsule.

8. The composition of claim 1 wherein the bisacodyl means comprises from about 0.5 mg to about 15 mg of bisacodyl wherein the bisacodyl is in a self-emulsifying or self-dispersing lipid solution.

9. The composition of claim 8 wherein the bisacodyl means is encased in a soft gelatin capsule.

10. The composition of any of claims 1, 3, 5, 6, 7 or 9 wherein the delivery means comprises a pH-sensitive enteric material which dissolves at a pH of from about 6.5 to about 7.

11. The composition of claim 3 or 9 wherein the delivery means comprises a pH-sensitive enteric material which dissolves at a pH of about 7.

12. A method for providing laxation for humans and lower animals in need thereof by peroral administration of a safe and effective amount of the composition of claim 1.

13. A method for providing laxation for humans in need thereof by peroral administration of a safe and effective amount of a composition as in any of claims 3, or 9 wherein the delivery means comprises a pH-sensitive enteric material which dissolves at a pH of from about 6.5 to about 7.

* * * * *